(12) United States Patent
Fermier et al.

(10) Patent No.: US 7,144,502 B2
(45) Date of Patent: Dec. 5, 2006

(54) CHROMATOGRAPHY SYSTEM WITH GRADIENT STORAGE AND METHOD FOR OPERATING THE SAME

(75) Inventors: Adam Fermier, Easton, PA (US); Kelly Swinney, Bethlehem, PA (US)

(73) Assignee: Johnson & Johnson, New Brunswick, NJ (US)

( * ) Notice: Subject to any disclaimer, the term of this patent is extended or adjusted under 35 U.S.C. 154(b) by 245 days.

(21) Appl. No.: 10/861,176

(22) Filed: Jun. 4, 2004

(65) Prior Publication Data
US 2005/0269264 A1    Dec. 8, 2005

(51) Int. Cl.
  *B01D 15/08*    (2006.01)
(52) U.S. Cl. ............... 210/198.2; 210/656; 210/659; 210/101
(58) Field of Classification Search ............ 210/635, 210/656, 659, 101, 198.2; 422/70
  See application file for complete search history.

(56) References Cited

U.S. PATENT DOCUMENTS

| | | | |
|---|---|---|---|
| 5,071,547 A * | 12/1991 | Cazer et al. ............ | 210/198.2 |
| 6,299,767 B1 | 10/2001 | Dourdeville | |
| 6,613,224 B1 | 9/2003 | Strand | |
| 2002/0017484 A1 | 2/2002 | Dourdeville | |
| 2003/0118459 A1* | 6/2003 | Gerhardt et al. ............ | 417/390 |

OTHER PUBLICATIONS

Cappiello, Achille et al., Variable-Gradient Generator for Micro-and Nano-HPLC, Anal. Chem. 2003, pp. 1173-1179.
Xiang, Yanqiao et al., Elevated-temperature ultrahigh liquid chromatography using very small polybutadiene-coated nonporous zirconia particles, Journal of Chromotography A, 2003.
Wu, Naijun et al., Practical aspects of ultrahigh pressure capillary liquid chromatography, Journal of Chromatography A, 2001.
MacNair John E. et al., Ultrahigh-Pressure Reversed-Phase Capillary Liquid Chromatography: Isocratic and Gradient Elution Using Columns Packed with 1.0-μm Particles, Anal Chem, 1999.
MacNair, John E. et al., Ultrahigh-Pressure Reversed-Phase Liquid Chromatography in Packed Capillary Columns, Anal. Chem., 1997.
Cintron, Jose M. et al, Organo-silica nano-particles used in ultrahigh-pressure liquid chromatography, The Analysist 2002.

* cited by examiner

*Primary Examiner*—Ernest G. Therkorn
(74) *Attorney, Agent, or Firm*—Darby & Darby (57) ABSTRACT

In accordance with one aspect of the present invention, an ultra-high pressure chromatography system (UHPLC) is provided and includes a high pressure chromatography arrangement of equipment (HPLC system) as well as a UHPLC module for converting the HPLC system into the UHPLC system. One exemplary module includes a gradient storage column fluidly connected to the HPLC equipment in a post injector manner such that an injection plug can be selectively delivered and stored, in an inverted manner, therein at low pressures, while stored injection plug (gradient) is delivered to an analytical column using higher pressures for chromatographic separation.

18 Claims, 10 Drawing Sheets

*Standard HPLC System*
Flow rate = 1 mL/min

Gradient Storage Column
Flow rate = 1mL/min
GS i.d. = 0.01"
GS length = 50 m

Gradient Storage Column System

Standard HPLC System

FIG. 7

CHROMATOGRAPHY SYSTEM WITH GRADIENT STORAGE AND METHOD FOR OPERATING THE SAME

TECHNICAL FIELD

The present invention relates to a chromatography system, and in particular to a chromatography system with a gradient storage configuration as a means to run chromatographic separations and a method for operating the same.

BACKGROUND

Separation science is a universal technique that benefits most scientists. Chromatographic separations provide a means to determine to what extent a reaction has yielded the desired products, to monitor impurities and dissolution profiles, and to study degradation pathways in drug products. Disadvantageously, chromatographic separations are relatively long and tedious processes with analysis times up to approximately one (1) hour or more. Another problem associated with conventional chromatographic separations is the method development time. Screen multiple columns, materials and instruments to achieve optimal separation is labor intensive.

There are a number of types of chromatography systems and generally one way of classifying the types is by operating pressures required to load and move a gradient through an analytical column. For example, chromatography systems are available in gas and liquid form and also at various pressures, such a low pressure systems, high pressure system and ultra-high pressure systems.

One of the disadvantages of conducing ultra-high chromatographic separation is that the equipment must be carefully selected and arranged such that the individual components can withstand the pressures generated in such an operation. This has been a major obstacle in providing an ultra-high pressure chromatography system that is constructed to withstand ultra-high temperatures of greater than 5,000 psi and upwards to 60,000 psi. More specifically, the equipment that is used in a standard LC system is often times unable to be used in a UHPLC setting since it is unsuitable for such an environment and/or is unable to properly function in this type of environment.

For example, a UHPLC pump that can be operatively connected to the solvent reservoir is generally not commercially available as well as one that is capable of gradient elution is likewise not available. Furthermore, performing injection under ultra-high pressures in a conventional LC system requires that the injector be able to withstand such pressures. Unfortunately, commercial injectors can not handle the ultra-high pressures and thus, they are unable to load the injection plug onto the analytical column under the desired ultra-high pressures. Alternatively, static-split flow injectors that can be used in place suffer from a number of disadvantages also, namely, that these type of injectors are of a manual operation type and they operate such that the injected amount is dependent upon the injection pressure and duration of time that the pressure is applied. As a result, the injection volume is difficult to control and estimate. Another challenge concerns the construction of the columns that are used in an UHPLC setting and the dimensions of the columns have to be tailored to permit efficient loading at the desired pressures.

In addition, high performance liquid chromatography (HPLC) has traditionally been performed in columns packed with 3 or 5 μm particle diameters. The internal diameter of these columns is typically between 2 and 4.6 mm, although smaller column diameters are gaining popularity. High separation efficiency with a concomitant gain in analysis time is achieved by reducing particle size and chromatographic packing materials with diameters in the range of 1 μm are now commercially available. However, the use of such materials imposes a great demand on the column inlet pressures that are required to drive the mobile phase through the chromatographic column and since these pressures are greater than those commonly provided by most commercially available pumping devices, the use of such materials is very difficult in a HPLC application. The problem is augmented by the fact that the optimum linear velocity is also dependent on the inverse of the particle diameter, and therefore, the required pressure to operate at optimum velocities is inversely proportional to the cube of the particle diameter.

In an effort to avoid the use of pumping devices, capillary electrochromatography (CEC) has been used to drive the mobile phase through a packed structure, even with submicron particles. However, CEC has presented several problems, including the column fabrication and its reproducibility, and the demands on the packing material to properly participate in the pumping mechanism via electroosmosis while serving as the stationary phase simultaneously, among others.

It is therefore desirable to provide an alternative LC system configured as a UHPLC system that has the ability to perform separations with very high efficiencies and is constructed in a cost effective manner.

SUMMARY

In accordance with one aspect of the present invention, an ultra-high pressure chromatography system (UHPLC) is provided and includes a conventional high pressure chromatography arrangement of equipment (HPLC system) as well as a UHPLC module for converting the HPLC system into the UHPLC system.

A typical HPLC arrangement includes: (1) at least one solvent reservoir maintaining an associated solvent and preferably, there are more than one solvent reservoirs with the number of solvent reservoirs being equal to the number of solvents; (2) at least one high pressure pump that is operatively coupled to the at least one solvent reservoir for transporting the solvent; (3) an injector disposed downstream of the at least one solvent reservoir for receiving the associated solvent or a gradient constituting a mix of several solvents; and (4) at least one analytical column disposed downstream of the injector for performing separation on an injection plug that is delivered thereto by the injector. A first conduit is disposed between the injector and the at least one analytical column.

One exemplary UHPLC module includes (1) a first valve disposed within the first conduit; (2) a gradient storage column fluidly connected to the first conduit and operatively coupled to the first valve so that the injection plug can be selectively delivered and stored therein; and (3) an ultra-high pressure pump operatively connected to the gradient storage pump for loading the stored injection plug onto the analytical column for separation thereof.

During loading of the injection plug onto the analytical column, all equipment upstream of the first valve (e.g., the injector and the high pressure pump) is shielded from ultra-high pressures generated by the ultra-high pressure pump.

Thus, the present UHPLC system and module provides an approach to use a gradient storage configuration as a means to run chromatographic separations. The configuration enables the use of precision gradient pumps to generate a gradient mobile phase for storage and a lesser performance pump (even operating in constant pressure mode) to dispense the pre-formed gradient for the separation analysis. In such a manner, multiple separations can be performed simultaneously or in series using a single set of high performance/precision pumps capable of forming gradients, one common bulk solvent pump with lesser precision, and multiple gradient storage columns or configurations. Also, by implementing the gradient storage concept and replacing the lesser performance pump with an ultra-high pressure pump (>5,000 psi), the UHPLC system can be constructed that allows gradient mobile phase systems to be generated and stored at low pressures, while the stored gradient is delivered using higher pressures (>5,000 psi) for chromatographic separation. In addition, the gradient storage design isolates the sample injector from the ultra-high pressure source, allowing commercially available injection valves, commonly used with standard HPLC system and unable to withstand pressures greater than 5,000 psi, to be used.

BRIEF DESCRIPTION OF THE DRAWING FIGURES

The foregoing and other features of the present invention will be more readily apparent from the following detailed description and drawings of illustrative embodiments of the invention wherein like reference numbers refer to similar elements throughout the several views and in which.

DETAILED DESCRIPTION OF PREFERRED EMBODIMENTS

Ultra high pressure liquid chromatography (UHPLC) has emerged as a viable approach to drive the mobile phase through columns packed with very small packing materials (<2 μm). The use of very high pressures should allow the use of column lengths typically utilized in HPLC while decreasing particle diameter, avoiding the current practices of decreasing the column length as the particle diameter is reduced. Accordingly, a UHPLC system holds the prospects of overcoming the aforementioned disadvantages and deficiencies associated with the conventional LC systems, including HPLC systems and CEC systems. The present invention is directed to providing a viable UHPLC system that can be widely commercially distributed and can offer high efficiency separation.

Figure 1:
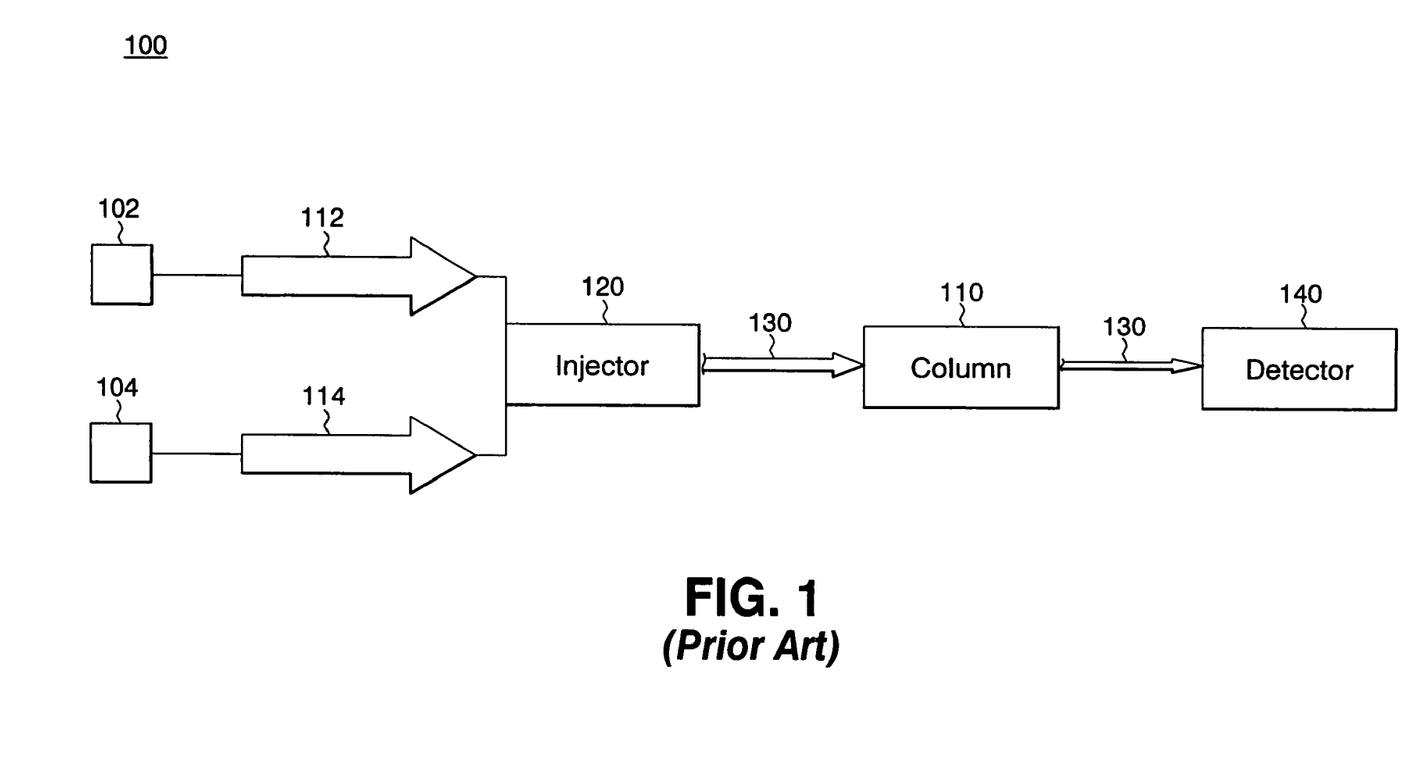
FIG. 1 is a schematic diagram of a conventional high performance chromatography system (HPLC) that is incorporated and/or converted into an ultra-high performance chromatography system UHPLC system of the present invention.

FIG. 1 is a schematic figure of a traditional high performance chromatography system (HPLC) 100 that includes at least two pressurized solvent reservoirs 102, 104 for delivering solvents A and B, respectively, in the form of a gradient phase to a column 110. It will be appreciated that system 100 could contain only one solvent reservoir for delivering a single solvent to the column 110. The flow rates of the solvents A and B into the column 110 is adjusted by a series of pumps 112, 114 that are associated with reservoirs 102, 104 and thus with solvents A and B, respectively. In other words, a first pump 112 is operatively coupled to the solvent reservoir 102 and is configured to pump a quantity of solvent A at a controllable flow rate. In a traditional HPLC system, the first pump 112 is of a type that is constructed and designed to handle normal or standard HPLC pressures, which are equal to or less than 5,000 psi. Similarly, the second pump 114 is identical or very similar to the first pump 112 in that it is of the type that is intended to be used in applications of less than or equal to 5,000 psi.

The first and second pumps 112, 114 are part of an overall programmable system in that the gradient profile of the sample can be inputted by a user resulting in the pumps 112, 114 being operated to produce the inputted, desired gradient sample profile that is injected or otherwise delivered to the column 110. For example, one type of gradient profile is one in which the gradient is transitioned from 0% solvent A to 100% solvent A over 10 minutes, while at the same time, the gradient is transitioned from 100% solvent B to 0% solvent B over the same 10 minute time period.

Each of the pumps 112, 114 is operatively coupled to an injector 120 that is designed to receive the gradient or mobile that is being delivered through conventional conduits (tubing) or the like to the injector 120. The injector 120 is of the type that can receive and deliver the gradient or mobile phase through a main conduit 130 to the column 110 under high pressure conditions (<5,000 psi).

A standard detector 140 is provided downstream of the injector 120 and more particularly at one end of the main conduit 130 which is connected at its other end to the injector 120. Any number of different detectors 140 can be used including but not limited to: ultraviolet UV, UV-VIS, fluorescent, refractive index (RI), chemical ion, evaporative light scattering (ELSD), LC-MS (HPLC-Mass Spectrometry), etc. One exemplary type of detector 140 is an ultra-violet detector for detecting the absorbance data from the column 110.

According to the present invention, a standard HPLC system, such as system 100, illustrated in FIG. 1 is converted into a device that operates at increased, higher internal pressures. For example, a group of chromatography systems (LC systems), other than the HPLC system described above, can be described and classified as being either: (1) VHPLC which stands for very high pressure LC; (2) UHPLC which stands for ultra-high pressure LC; and (3) UPLC which stands for ultra performance LC. All of the above are LC systems with increased pressure capabilities (>5,000 psi) that are compatible with columns of standard length (i.e., 150 mm) packed with small (<2 μm) diameter particles. As used herein, HPLC refers to an LC system that operates at high pressures which are defined as being below 5,000 psi and UHPLC refers to an LC system that operates at ultra-high pressures which are defined as being pressures above 5,000 psi and can be significantly higher pressures, such as 60,000 psi.

One area of application that is particularly suited for UHPLC systems is the area of drug development. By using small diameter particles and operating parameters associated with a UHPLC application, one can realize increased pack capacity through increased column efficiency. For example within the area of drug development chromatographic testing can be used in experiments that are associated with: (1) drug chemistry/impurity profiling—major degradation products, UHPLC-MS and UHPLC-NMR; (2) method development—decreased method development time, verify complete separation of all sample components before method validation; and (3) fast separations/PAT—high throughput screening/assays.

According to one exemplary embodiment for a UHPLC system according to the present invention, the UHPLC module pump that is used therein is constructed so that it can operate under ultra-high pressures on the order of pressures equal to or less than about 60,000 psi. In addition, the pump should also be a programmable pump that has gradient capability. While the injector associated with the present system can be of the type that can operate in ultra-high pressure environments and therefore, the injector should be able to withstand pressures of equal to or less than 60,000 psi, it will also be appreciated that the injector can be and is preferably of standard type that is intended for use in a standard HPLC environment (<5,000 psi). The injector is of the type that can inject volumes greater than or equal to about 100 nL. The column is of the type that contains very small particles, e.g., diameter of less than or equal to 2 µm and it has an inner diameter that is greater than 1.0 mm. One exemplary detector is a UV-Vis DAD detector that has a cell volume of from about 40 to about 500 nL.

There are number of challenges to constructing such a UHPLC system, with many of the challenges concerning shortcomings in the specifications and intended operating conditions of the equipment. For example, a UHPLC pump is not commercially available since conventional HPLC systems use traditional HPLC pumps which are not capable of operating at UHPLC pressures (ultra high pressures) that are needed in a UHPLC application. Another challenge is the selection of an appropriate or suitable injector that can be used to inject or deliver the sample (gradient or mobile phase) after it is received from the various solvent reservoirs by means of the pumps. In other words, the injector must be capable of performing injection under ultra-high pressures and unfortunately, commercial injectors can not handle these ultra-high pressures. In addition, another problem is that a commercial UHPLC pump capable of gradient elution is not available. In other words, equipment is not generally available to provide an effective and commercially reproducible UHPLC that operates at the associated ultra-high pressures.

Figure 2:
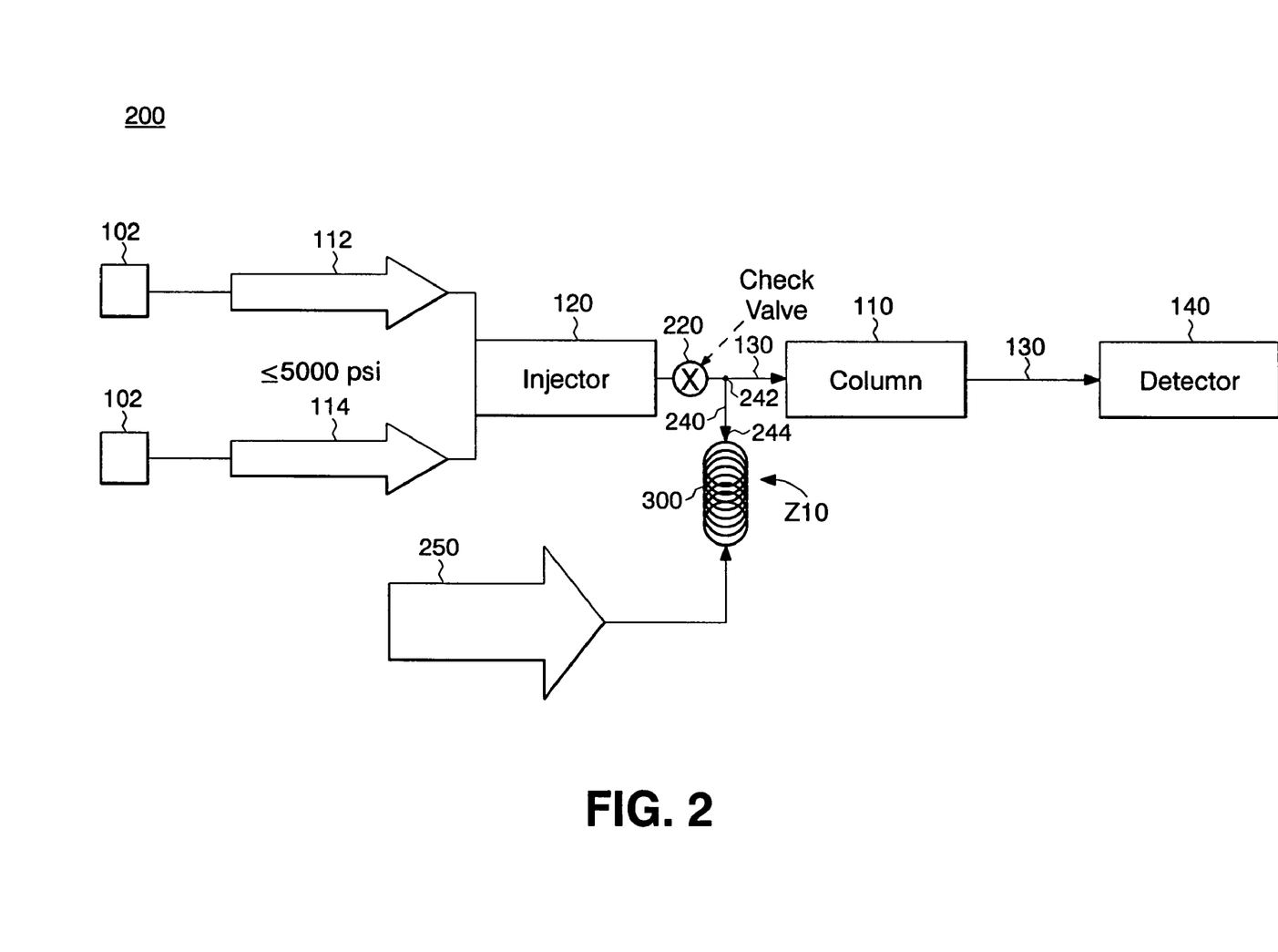
FIG. 2 is a schematic diagram of an ultra-high performance conversion kit or module, according to a first embodiment, operatively connected to the HPLC of FIG. 1 enabling storage of a gradient mobile phase.

In accordance with the present invention, an ultra-high pressure LC module is provided as part of the chromatographic system or for interfacing therewith to provide UHPLC performance. FIG. 2 illustrates an exemplary UHPLC system 200 that includes an UHPLC module 210, according to a first embodiment, that is interfaced with a conventional HPLC set-up that is generally shown at 100. In the UHPLC system 200, one or more and preferably two or more solvent reservoirs 102, 104 are provided to each store and contain respective solvents A and B in this case. It will be appreciated that while two solvents are shown in FIG. 2, more than two solvents can be provided in a parallel relationship for injection to the injector 120, with each solvent being associated with its own pump for pumping the solvent at a controllable flow rate to the injector 120.

Each of the pumps 112, 114 is operatively coupled to the injector 120 that is designed to receive the gradient or mobile that is being delivered through conventional conduits (tubing) or the like to the injector 120. The injector 120 is of the type that can receive and deliver the gradient or mobile phase through a main conduit 130 to the column 110 under high pressure conditions. Since the UHPLC module 210 permits the remaining equipment of the system 200 to be in the form of commercially available HPLC equipment, the pumps 112, 114 do not have to be of the type that are constructed to withstand ultra high pressures (>5,000 psi) but rather, the pumps 112, 114 are HPLC pumps that operate at pressures less than 5,000 psi and the injector 120 is likewise of the type that is intended to operate at only high pressures as opposed to ultra high pressures.

To interface the UHPLC module 210 with the HPLC equipment, a valve and conduits are provided to deliver the gradient or mobile phase to the module 210 in a post injector manner (i.e., downstream of the injector). To accomplish this, the first conduit 130 that is provided between and fluidly connects the injector 120 to the column 110 is modified and more particularly, the UHPLC module 210 interfaces along a point thereof. In other words, the first conduit 130 is connected at one end to the injector 120 and at its opposite end to the column 110. The first conduit 130 is modified by providing a check valve 220 downstream of the injector 120 but upstream of the column 110. The check valve 220 is operable to either permit or prevent fluid from flowing between the injector 120 and the first conduit 130. The check valve 220 can be of a conventional type that is intended for use in HPLC applications and can be operatively connected to an automated, programmable system so that the operation thereof can easily be controlled and/or modified. It will be appreciated that the check valve 220 is installed between the injector 120 and the column 110 so as to permit isolation of the HPLC (i.e., the injector 120 and pumps 112, 114) from ultra-high pressures when performing UHPLC.

The UHPLC module 210 is interfaced with the first conduit 130 through a second conduit 240 that is operatively connected at one end 242 thereto and at its other end 244 to a gradient storage column 300. One exemplary gradient storage column 300 is in the form of a column or tubing that is manipulated into a loop (series of adjacent loops) so as to conserve the amount of space that is required by the gradient storage column 300. The gradient storage column 300 is configured to receive the gradient or mobile phase from the injector 120 under normal (standard) HPLC pressures of less than or equal to about 5,000 psi. The gradient or mobile phase that is transported through the first conduit 130 by means of the operation of the injector 120 can also be referred to as an injection plug. Since the gradient storage column 300 is merely a storage column for the gradient or the mobile phase prior to it being pumped under ultra-high pressures, as explained below, to the column 110, the gradient or mobile phase is stored in an inverted manner. In other words, if it desired for the injection plug to be loaded into the main conduit 110 to start with 100% solvent A and 0% solvent B, then the injection plug is stored by loading the injection plug starting with 0% solvent A and 100% solvent B since the portion of the injection plug that is first loaded into the gradient storage column 300 is the last portion of the plug that is loaded into the main analytical column 110.

The check valve 220 is at least positionable in two positions, namely, a first position where the valve 220 is open and fluid can flow between the injector 120 and the check valve 220 and into the gradient storage column 300 and a closed position where the conduit 130 is closed off between the injector 120 and the check valve 220 (upstream of the check valve 220), whereby the injector 120 and all equipment upstream therefrom is not in communication with the gradient storage column 300.

To load the gradient or mobile phase onto the gradient storage column 300, the check valve 220 is opened and the pumps 112, 114 are operated so that the solvents stored in the reservoirs are delivered to the injector 120 at the appropriate ratios to form the injection plug (in an inverse manner) and then the injection plug is delivered, under normal pressures (<5,000 psi) by action of the injector 120 to the gradient storage column 300. It will be appreciated that the back pressure generated by the gradient storage column 300 draws the injection plug therein as opposed to the injection plug traveling through the conduit 130 from the injector 120 and into the column 110. Thus, the back pressure permits the loading of the injection plug to proceed as a result of merely positioning the check valve 220 in the proper position (open position). The pumps 112, 114 continue to operate until the injection plug is loaded into the gradient storage column 300.

After the injection plug has been loaded onto the gradient storage column 300, the system 100 is manipulated so as to permit the stored injection plug to be loaded onto the head of the analytical column 110. This is accomplished by setting the check valve 220 in the closed position such that the conduit 130 upstream of the check valve 220 is closed off, while the conduit 130 downstream of the check valve 220 is open and more particularly, the injection plug can travel through a conduit section that extends from the switching valve 230 to the column 110 is open and a fluid pathway is defined from the gradient storage column 300 to the column 110 to permit the stored gradient to be delivered from the column 300 to the main column 110 in a controlled manner. Advantageously, the pump 250 does not have to be a high precision pump intended for an LC application, but rather can be more a standard (lower precision) ultra-high pressure pump.

The UHPLC module 210 thus includes the pump 250 that is operatively connected to the gradient storage column 300 for delivering the stored injection plug to the column 110 under ultra high pressures. The pump 250 is preferably an ultra-high pressure pump that is constructed for applications in ultra-high pressure environments. Thus, the pump 250 is of the type that operates at pressures greater than 5,000 psi and typically, the pump 250 operates at ultra-high temperatures, such as ultra-high pressures up to about 50,000 psi. However, it will be appreciated that the pump 250 is not limited to such operating pressures but is of the type that is classified as an ultra-high pump that is suitable for use in an ultra-high pressure chromatography. However, it will be understood that the pump 250 can be a standard pump that is suitable for delivering and loading the stored injection plug onto the head of the analytical column 110 to begin the separation process. This embodiment is discussed in more detail below with respect to FIG. 4.

The UHPLC module 210 thus is relatively simple in construction yet is very effective in operation and permits conversion of any commercial HPLC system into an operable UHPLC system that does not require replacement of the existing HPLC equipment, such as the injector 120 and pumps 112, 114. It will be appreciated that by positioning the check valve 220 in the closed position, the HPLC equipment, namely, the injector 120 and the pumps 112, 114, are isolated from the ultra high pressures generated by the ultra-high pressure pump 250 to deliver the stored gradient under ultra-high pressure to the column 110. If the check valve 220 was not present, the HPLC equipment would be exposed to pressures that far exceed their normal HPLC operating pressures, and as a result, the equipment is exposed to unnecessary pressures which cause wear and tear and can potentially damage the system. Advantageously, the HPLC equipment, e.g., the pumps 112, 114 and injector 120, can be used in the present UHPLC system 100 and the equipment does not require modification and/or replacement and thus, there are no associated costs with having to modify the equipment for use in the present system. In other words, off-the-shelf HPLC equipment can be used in the present UHPLC system 100 as a result of the UHPLC module 210. By using an ultra-high pressure pump 250 as part of the module 210, the injection plug is delivered to the main analytical column 110 under ultra-high pressures and therefore, all of the aforementioned advantages that are obtained with an UHPLC system are achieved and realized with the present system.

It will be understood that the UHPLC module 210 acts as a conversion kit for converting a HPLC system into an UHPLC system. Thus, any existing HPLC system can be converted by simply modifying the conduit 130 between the injector 120 and the main column 110. More specifically, the conduit 130 is modified by incorporating the gradient storage column 300 therewith and adding the switch 230 to controllably and selectively deliver the injection plug from the injector 120 to the main analytical column 110. Any equipment that is downstream of the gradient storage column 300 must be able to withstand ultra high pressures and therefore, in the present arrangement, the check valve 220 must be of the type that can withstand ultra high pressures since the main analytical column 110 is capable of withstanding ultra high pressures.

Figure 3:
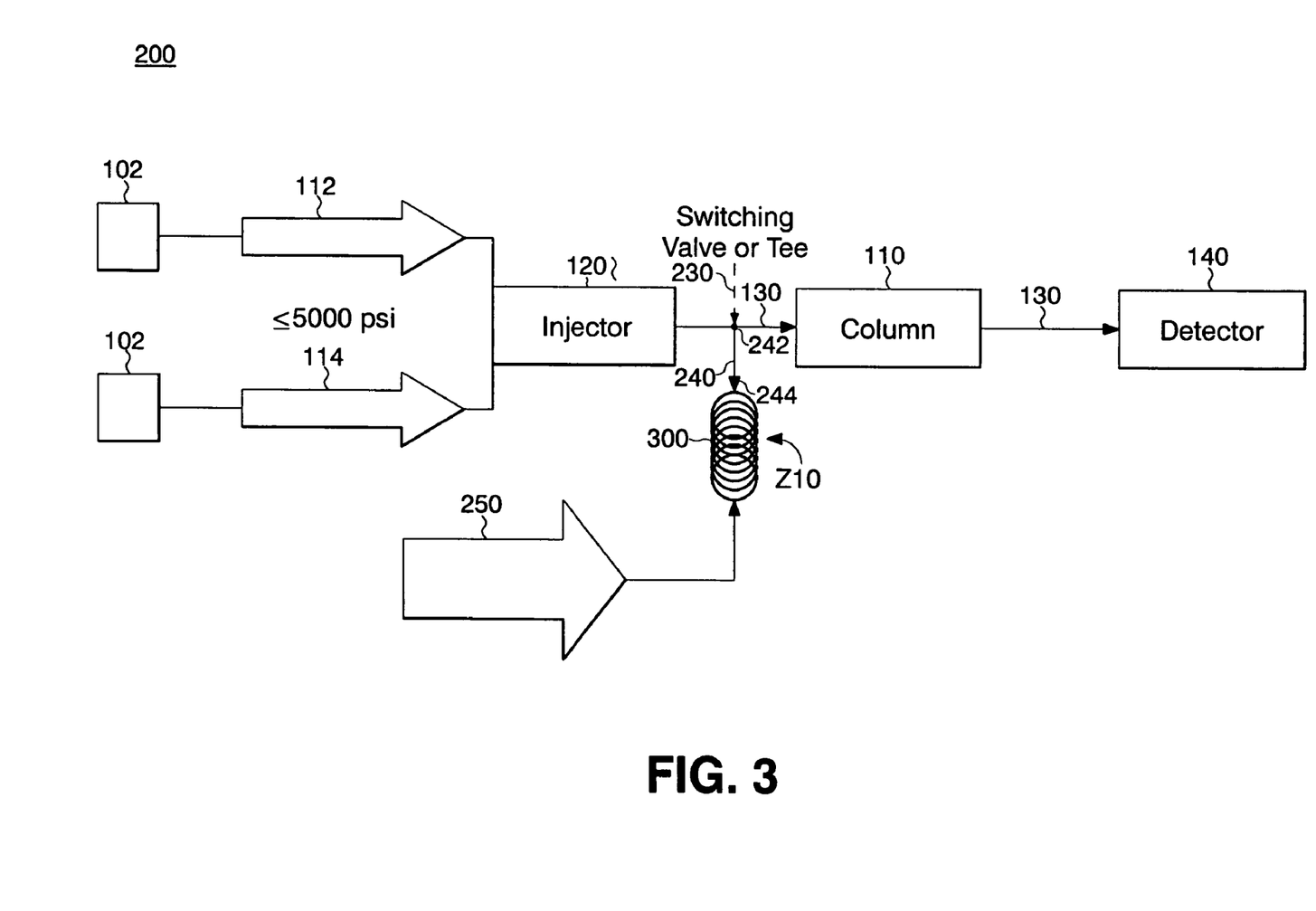
FIG. 3 is a schematic diagram of an ultra-high performance conversion kit or module, according to a second embodiment, operatively connected to the HPLC of FIG. 1 enabling storage of a gradient mobile phase.

Now referring to FIG. 3 in which a second embodiment of the UHPLC module 210 is shown. The second embodiment is almost nearly identical to the first embodiment with the exception that the check valve 220 is replaced with a switching valve or tee 230. The switching valve or tee 230 is disposed along the conduit 130 between the injector 120 and the column 110. Similar to the check valve 220, the switching valve or tee 230 can be placed into at least several positions for routing the flow path of the injection plug. More specifically, the switching valve or tee 230 can be placed in a first position in which a flow path is defined between the injector 120 and the gradient storage column 300 and a second position in which a flow path is defined between the gradient storage column 300 and the column 110 and the conduit section upstream of the switching valve or tee 230 is closed off to prevent the stored injection plug from being delivered back to the injector 120 and thereby isolate the gradient storage column 300 and the column 110.

Advantageously and according to some embodiments, the switching valve (tee) 230 can be in the form of a standard tee that is used in HPLC applications, thus eliminating the need for a low dead volume switching valve that can withstand ultra high pressures (>5,000 psi) since the high back pressure of the UHPLC column is large enough to prevent flow splitting. However, the switching valve 230 can be an ultra-high pressure valve as opposed to a tee. The switching valve or tee 230 can be, as previously mentioned, a conventional switching valve and it is constructed so that it controls the extent to which each of the first and second conduits 130, 240 are open and the precise flow path of the fluid depends upon the position of the switching valve 230. More specifically and will be described in greater detail below, the switching valve 230 can be positioned in a first position in which the second conduit 240 is closed off from the first conduit 130 in that the gradient or mobile phase is delivered by the injector 120 to the column 110. In this first position, the system actually is functioning purely as an HPLC system since the UHPLC loop is taken off-line so to speak.

When the switching valve 230 is manipulated to a second position, the portion of the first conduit 130 upstream of the switching valve 230 is placed in fluid communication with the second conduit 240, thereby permitting the gradient or mobile phase to flow from the first conduit 130 into the second conduit 240 toward the gradient storage column 300. This second position is associated with a loading operation of the gradient or mobile phase into the gradient storage column 300 since the gradient or mobile phase is delivered to the gradient storage column 300 as opposed to being delivered downstream through the first conduit 130 to the main column 110. Alternatively and according to one exemplary embodiment, the switching valve 230 is a 6-port 20,000 psi Valco valve. However, it will be understood that the valve 230 can be of the type that can withstand even high pressures on the order of up to about 60,000 psi.

Figure 4:
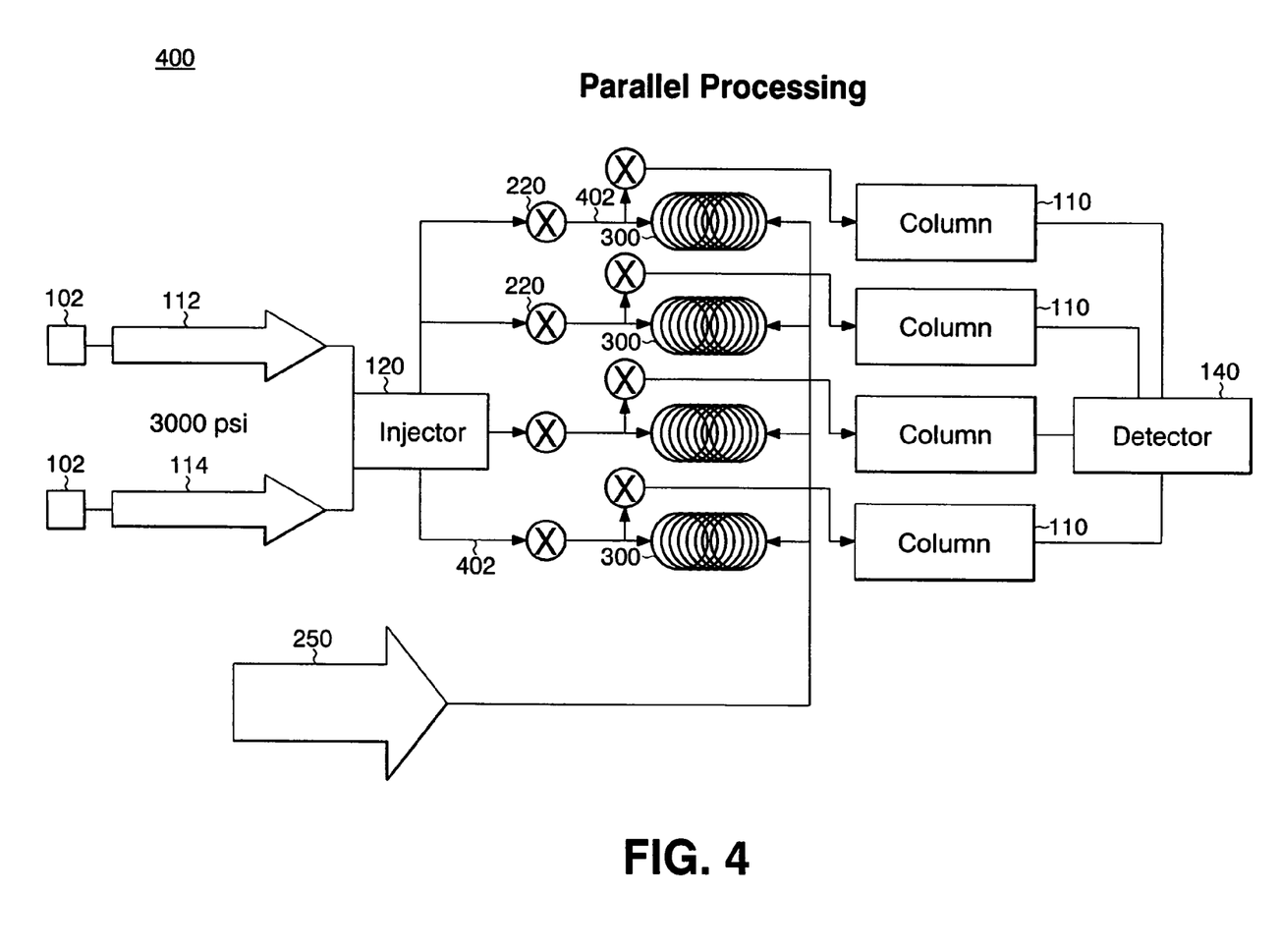
FIG. 4 is a schematic diagram of an ultra-high performance chromatography system with an ultra-high performance conversion kit included as a part thereof and constructed and arranged to permit parallel chromatography processing.

FIG. 4 illustrates yet another embodiment in which parallel processing of the sample is provided as is desirable in some applications. In a parallel processing arrangement, a plurality of gradient storage columns 300 are arranged parallel with respect to each another and the analytical main columns 110 are arranged parallel with respect to one another. More specifically, FIG. 4 shows an ultra-high pressure chromatography system 400 that has a number of similarities with the system 100 of FIG. 1. For instance, two or more solvent reservoirs 102, 104 are provided for holding at least a Solvent A, with each solvent reservoir 102, 104 having pumps 112, 114, respectively. As with the system 100, the pumps 112, 114 are standard HPLC pumps that operate at pressures less than about 5,000 psi, e.g., about 3,000 psi. Each of the pumps 112, 114 are associated with fluid conduits that are in fluid communication with the injector 120 such that a gradient or mobile phase of solvents A and B is delivered to the injector 120 and forms an injection plug.

The injector 120 is connected downstream thereof to a plurality of fluid connector conduits 402 such that the injection plug can be delivered to a selected fluid connector conduit 402 by manipulating a plurality of check valves 220 that are associated with and disposed at locations along the length of the fluid connector conduits 402. More specifically, one check valve 220 is associated with one of the fluid connector conduits 402. Each connector conduit 402 is connected at one end to the injector 120 and at the opposite end to one gradient storage column 300 with the check valve 220 being disposed fluidly downstream of the injector 120 and fluidly upstream of the gradient storage column 300. As with the system 100, the check valve 220 serves to isolate the HPLC equipment from the UHPLC equipment. It will be appreciated that the number of gradient storage columns 300 is preferably equal to the number of connector conduits 402.

In the event that it is not desirable to load all of the gradient storage columns 300 with an injection plug for storage thereof, before loading the stored injection plugs onto corresponding analytical columns 110, the user can simply instruct and position a number of check valves 220 in closed positions so as to effectively close off the respective fluid flow paths from the injector 120 to the corresponding gradient storage column 300. In other words, one or more of the gradient storage columns 300 can be taken off line relative to the common injector 120 and thus, only select gradient storage columns 300 and corresponding select main analytical columns 110 receive injection plugs and actively perform the separation process. Thus, not all of the pairs of columns 300, 110 need to be used but rather, a select number of pairs of columns 300, 110 can be used to receive and perform the separation process.

As with the system 100, each connection conduit 402 can include a switching valve or tee 230 as opposed to having a check valve 220 that is associated therewith and is intended for use in an ultra-high pressure environment. Operation of the switch valve 230 serves to direct the injection plug along a select fluid flow path such that when the switch valve 230 is in a first position, the injection plug is delivered to the gradient storage column 300 where it is stored and when the switch valve 230 is in a second position, the injection plug can be delivered from its stored location in the gradient storage column 300 to the main analytical column 110 where the separation process takes place.

It will be understood that the gradient storage column 300 and the main analytical column 110 are in fluid communication with each other such that the stored gradient or mobile phase (stored injection plug) can be delivered from the gradient storage column 300 to the column 110 and then ultimately to the common detector 140 which is in communication with each of the columns 110. As with the system 100, the stored injection plugs (gradients) are transported from their stored locations in the gradient storage columns 300 to the analytical columns 110 by action of the ultra-high pressure pump 250 which is operatively connected to each of the gradient storage columns 300. Accordingly, the parallel processing system 400 of FIG. 3 only requires the use of one ultra-high pressure pump 250 that is connected to each of the columns 300 as opposed to having multiple pumps 250 arranged in a one pump to one column 300 manner.

The system 400 permits parallel chromatography to be easily conducted. In other words, it permits loading multiple gradient storage columns 300 with the same and/or different solvent compositions or profiles to run the chromatography. When the same solvent composition or profile is used, the injector 120 and the associated valves can be operated to simply load one gradient storage column 300 with the solvent composition or profile and then subsequently loading the other gradient storage columns 300 with the same solvent composition or profile. Thus, the solvent composition or profile can be processed in a parallel manner and stored in a parallel manner in the gradient storage columns 300 before being delivered to respective analytical columns 110 where parallel chromatography (separation) is conducted.

By using one ultra-high pump 250, each of the stored gradients (injections plugs) can be delivered substantially simultaneously to their respective analytical columns 110 and then to the common detector 140. This design not only saves money by combining a number of instruments, thereby saving cost and space, but also allows for faster method development time and sample throughput by generating multiple chromatograms at once. This can be expected to reduce the sample throughput and method development times by at least a factor of 10 or more.

The same advantages outlined above with respect to the system 100 apply to the system 400 in that the design permits use of a number of HPLC components in an ultra-high pressure environment, with the HPLC components being shielded from the ultra-high pressures by action of the check valves 220. Thus, only ultra-high pressures are used to transport the injection plug to the column 110 as opposed to being required for transporting the gradient or mobile phase across the injector 120, thereby shielding the injector 120 from ultra-high pressures.

The use of multiple parallel gradient storage columns 300 permits two or more injections plugs to be stored in respective columns 300 before the ultra-high pressure pump 250 is operated to load the injection plugs onto their respective analytical columns 110 and then to the detector 140. By storing the injection plugs in separate gradient storage columns 300 and the independent control over the gradient storage column 300 and associated valve members, such as switching valve 230, permits selective control over which stored gradients (injection plugs) are transported to analytical columns 110 and it will be appreciated that the system 400 can be controlled such that the injection plugs can be delivered at different times. For example, injection plugs A and B can be transported at a first time to their respective columns 110, while injection plugs C and D can be transported at a second time to their respective columns 110. Of course, the injection plugs A–D can be delivered simultaneously to their respective columns 110.

In another aspect of the present invention, the pump 250 is not an ultra-high pressure pump but merely is a standard pump. In this embodiment, the gradient storage column 300 is not part of an ultra-high pressure LC module but rather is part of a parallel processing system in which injection plugs can be loaded and stored in a parallel manner prior to loading onto the analytical column 110. The stored injection plugs are loaded under standard pressures (HPLC pressures of less than 5,000 psi) as opposed to ultra-high pressures. In this embodiment, the gradient storage column 300 acts as a storage means for the gradient.

The present systems therefore provide a means for using a gradient storage configuration as a way to run chromatographic separations. This configuration enables the use of precision gradient pumps (HPLC equipment) to generate a gradient mobile phase for storage in the gradient storage column 300 and a lesser performance pump (UHPLC pump) 250 to dispense the pre-formed gradient to a conventional analytical column for separation analysis. In such a manner, multiple separations can be performed simultaneously or in series using a single set of high performance/precision pumps capable of forming gradients, one common bulk solvent pump with lesser precision, and multiple gradient storage columns or configurations. Also, by implementing the gradient storage concept and replacing the lesser performance pump with an ultra-high pressure pump (>5,000 psi), an ultra-high pressure liquid chromatography (UHPLC) system can be constructed that allows gradient mobile phase systems to be generated and stored at low pressures, while the stored gradient is delivered using higher pressures (>5,000 psi) for the chromatographic separation. In addition, the gradient storage design isolates the sample injector from the ultra-high pressure source, allowing commercially available injection valves, commonly used with standard HPLC systems and unable to withstand pressures greater than 5,000 psi, to be employed.

The present systems can generally be provided in the form of a conversion kit or UHPLC module that is configured to easily interface with an existing commercially available HPLC system in such a manner that requires no updating, replacement or modification of the HPLC equipment in order to operate under ultra-high pressures. Instead, the UHPLC equipment is merely operatively connected to the existing HPLC equipment as described above. Another advantage is that the present UHPLC system utilizes commercial autosamplers and detectors and is capable of programmable gradients and can easily be configured and offered as a fully automated system.

As previously mentioned, while ultra-high pressure liquid chromatography has emerged as a viable approach to driving mobile phases through columns that contain chromatographic packing materials with diameters in the range of 1 μm, these systems until now have utilized capillary columns to reduce flow rate and dissipate the presumed frictional heating of the mobile phase that is thought to occur when very high pressures are used in HPLC. The present inventors have discovered that non-capillary columns can in fact be used in a UHPLC system by configuring the system as described herein and by incorporating a UHPLC module (conversion kit) into the existing LC system as set forth in detail herein. It has been found that the use of very high pressures (ultra-high pressures) should allow the use of column lengths typically utilized in HPLC while decreasing particle diameter, thereby avoiding the current practices of decreasing the column length as the particle diameter is reduced.

One element of the gradient storage column design that advantageously is optimized is the inner diameter of the gradient storage column 300 in order to obtain the best possible UHPLC performance. Ideally, the use of a narrow or small inner diameter gradient storage column 300 increases the likelihood that the integrity of the gradient is preserved during storage. In practice, a minimum storage capacity of 2 mL is necessary for most applications. Ultimately a compromise has to be found between column inner diameter and length, while preserving the integrity of the stored gradient and providing the storage capacity necessary for practice.

To determine the effect of the gradient storage column's inner diameter on preserving the integrity of the stored mobile phase, a storage column was installed such that one end was connected to a set of standard HPLC pumps and the other to a detector. The pumps were programmed to generate a saw-toot gradient profile where the gradient was transitioned from 0% solvent A to 100% solvent A over 1 minute and then back to 0% solvent A over a 1 minute interval. This gradient profile was repeated 3 times. The resultant gradient profile was then analyzed using the UV absorbance detection. Finally, the gradient storage column 300 was removed and the pumps were connected directly to the detector. The same saw-tooth gradient profile was formed and analyzed providing a standard for which the gradient storage column profiles should be compared.

Figure 5A:
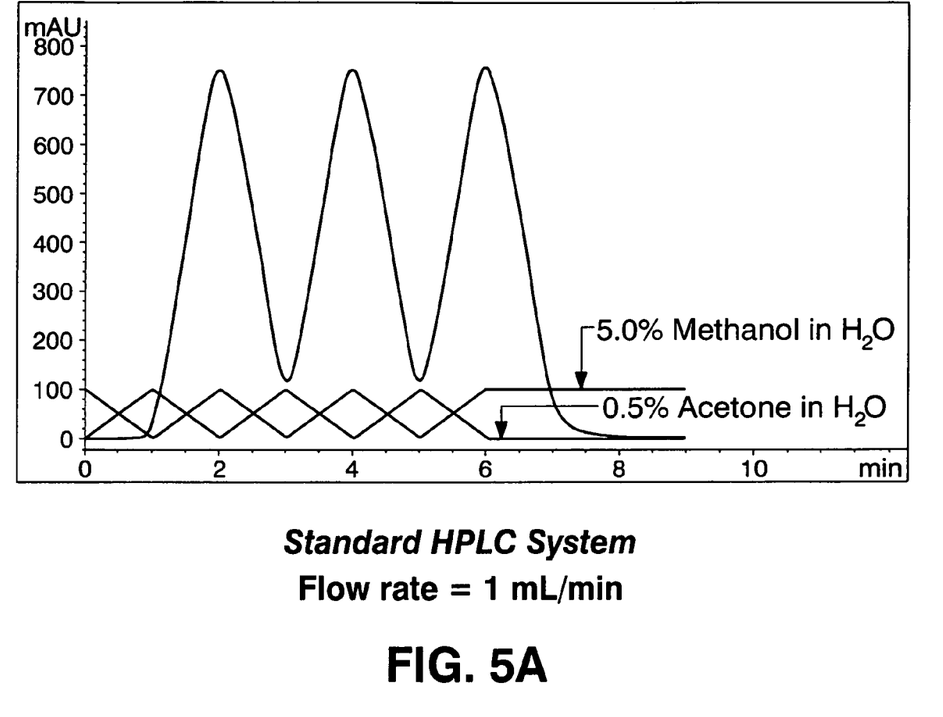
FIGS. 5A–C are schematic graphs showing results of a gradient storage column inner diameter experiment.
Figure 5B:
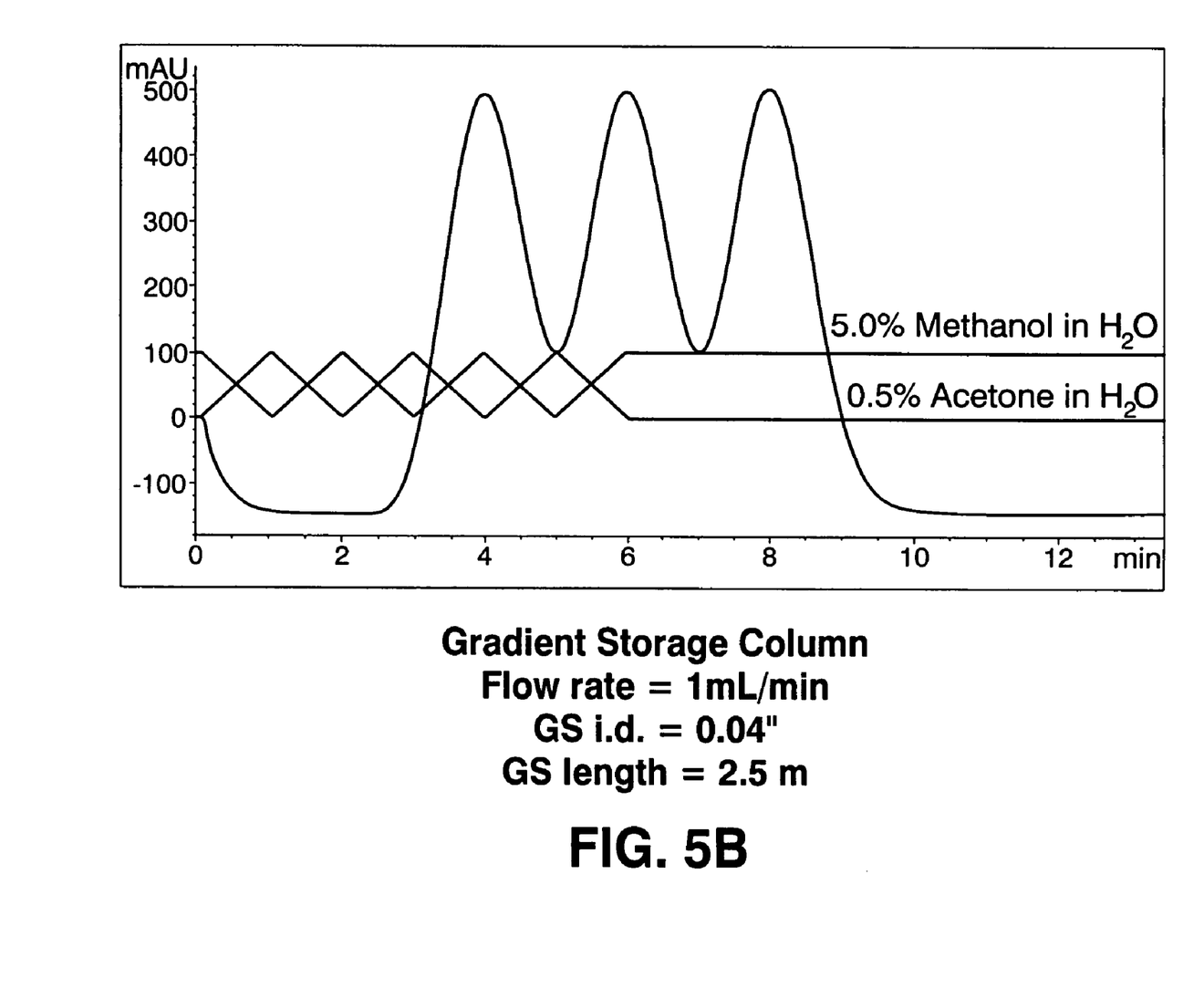
Figure 5C:
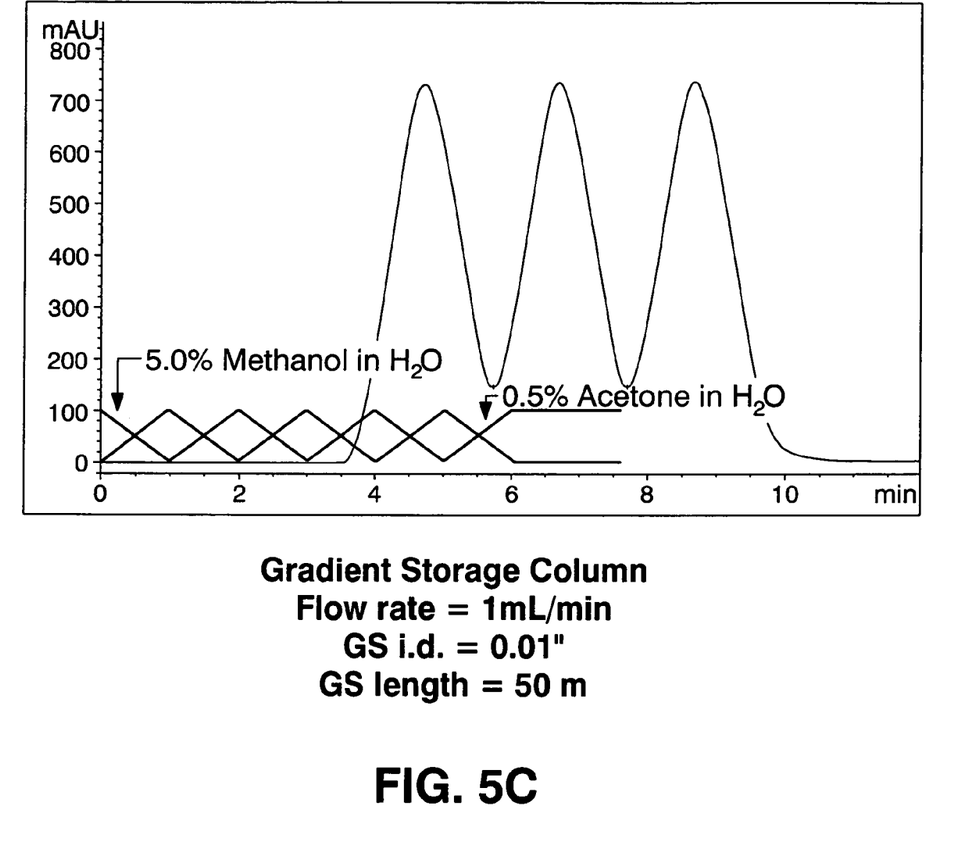

FIGS. 5A–C show the results of the gradient storage inner diameter investigation described above. The absorbance of acetone, a mobile phase additive present at a concentration of 5% v/v acetone/solvent A, was used as the indicator for determining the integrity of the mobile phase. FIG. 5A is the gradient profile produced by a standard HPLC operating with a 1 m/min flow rate. It will be appreciated that the peaks are very sharp and the troughs are very low. The peaks approach 800 mAU while the troughs plunge to approximately 100 mAU. The gradient profile of FIG. 5B was produced for a system equipped with a 0.04" inner diameter gradient storage column operating at a flow rate of 1 mL/min. Comparison of the gradient profile of the standard HPLC system (FIG. 5A) with that of the system equipped with the 0.04" inner diameter gradient storage column (FIG. 5B) indicates that appreciable mixing of the mobile phase occurs in the 0.04" gradient storage column reducing the integrity of the gradient. This was established by comparing the peak heights and troughs for the two systems. However, completion of the same experiment with a gradient storage column with an inner diameter of about 0.01" produced results that show that showed that the integrity of the mobile phase was maintained. Mixing was minimized by using a gradient storage column with an inner diameter four times smaller. This conclusion is drawn through comparison of peak heights and troughs of the results obtained with the standard HPLC setup and the 0.01" inner diameter storage column system as shown in FIG. 5C. More specifically, both sets of results has peak heights approaching 800 mAU and troughs of 100 mAU. However, other inner diameters are possible and for some applications an inner diameter between about 0.01" and 0.04" may be suitable. Thus, a column having an inner diameter of about 0.01" is merely exemplary and not limiting.

To further test the ability of an open tubular column to act as a s gradient storage column, a system was configured identical to the system shown in FIG. 1, with only one exception, namely, that the analytical columns was replaced with a 1000 psi back pressure regulator in order to eliminate the need for a multi-position small dead volume switching valve. In this experiment, a gradient mobile phase was loaded into the column and the eluted under formal pressures through the backpressure regulator and through a UV detector for analysis. Thus, in one embodiment, the gradient storage column is selected so that it contains about 0.01" inner diameter since an inner diameter in this range has the ability to maintain the integrity of the gradient profile. However, it will be appreciated that the inner diameter of the gradient storage column 300 can be outside of this value so long as the inner diameter of the column 300 preserves the integrity of the gradient profile and provides suitable results.

Figure 6A:
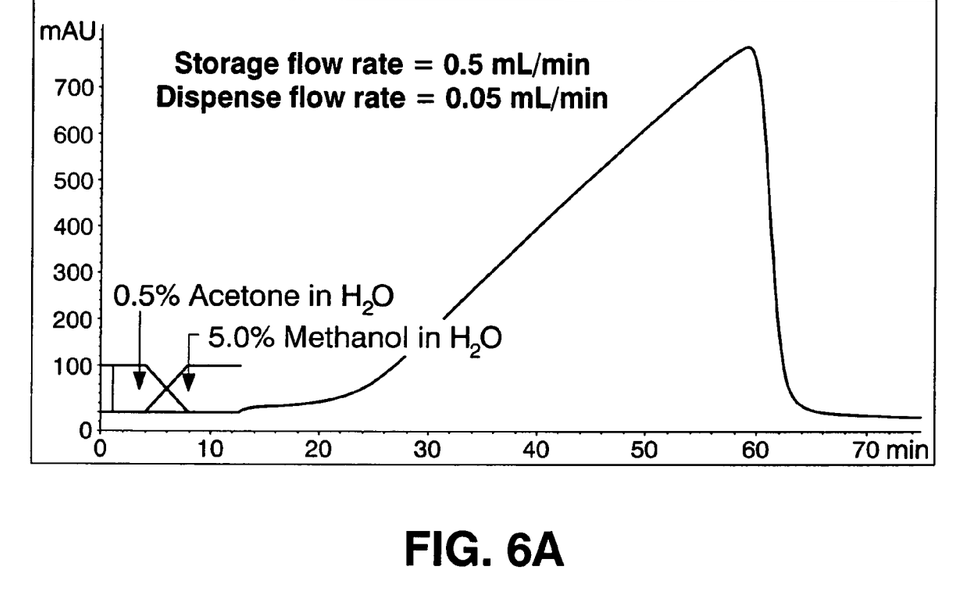
FIGS. 6A–B are schematic graphs of various gradient flow profiles.

The gradient flow profile present in FIG. 6A represents a gradient system that was stored at a flow rate of 0.5 mL/min and dispensed at a flow rate of 0.5 nL/min. The gradient was stored inverted starting with 100% 0.5% acetone in water/ 0% 5% methanol in water over minutes. The resultant gradient profile delivered to the detector was identical to that stored as indicated by the peak height which was approximately 800 mAU (sign of minimal mixing).

Figure 6B:
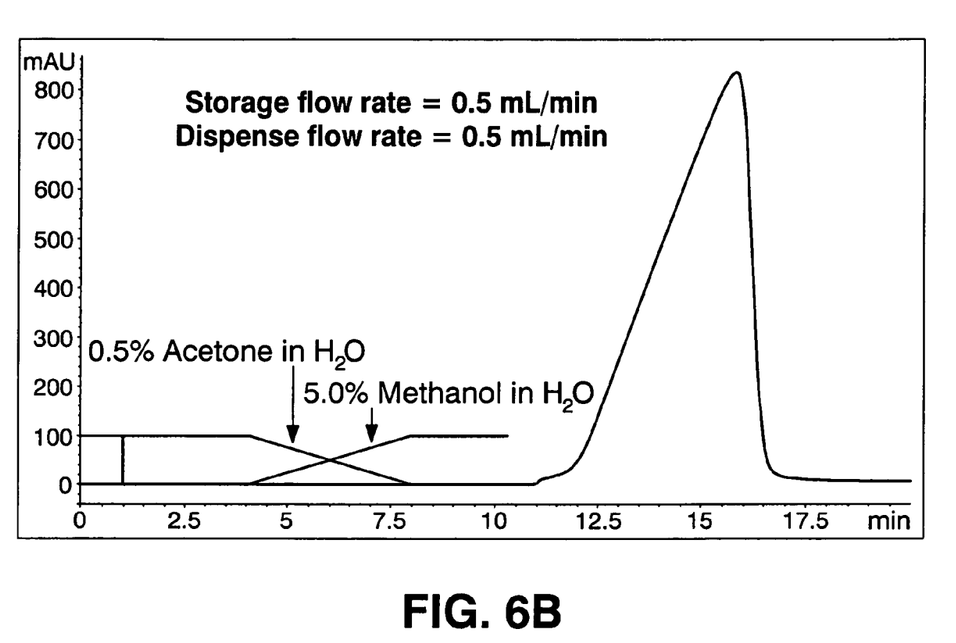

The gradient flow profile presented in FIG. 6B represents the same gradient system just described except that the dispensing flow rate was reduced by a factor of 10 to 0.05 mL/min. The resultant gradient profile composition determined by the detector was identical to that delivered as indicated by the peak height around 800 mAU except that due to the slower dispensing rate, the slope of the gradient profile was 10 times less. This investigation demonstrates that the gradient can be stored using flow rates reducing the amount of pre-injection time required for an analysis. Also, the results indicate that the longer storage time experienced by the mobile phase system due to the slower dispensing rate did not compromise the integrity of the gradient.

To determine if loading the injection plug into the gradient storage column 300 would have deleterious effects to the separation performance of the system, an isocratic analysis of urasil, acetophenone, and methyl benzoate was performed. Due to insufficient backpressure supplied by the 2.1 mm inner diameter analytical column, a multi-port valve was installed in place of the switching valve/tee 230. In this configuration, the isocratic mobile phase was loaded onto the gradient storage column 300 followed by the injection plug. The flow rate used and the time needed to push the injection plug onto the head of the storage column 300 was also optimized before the analysis.

Figure 7:
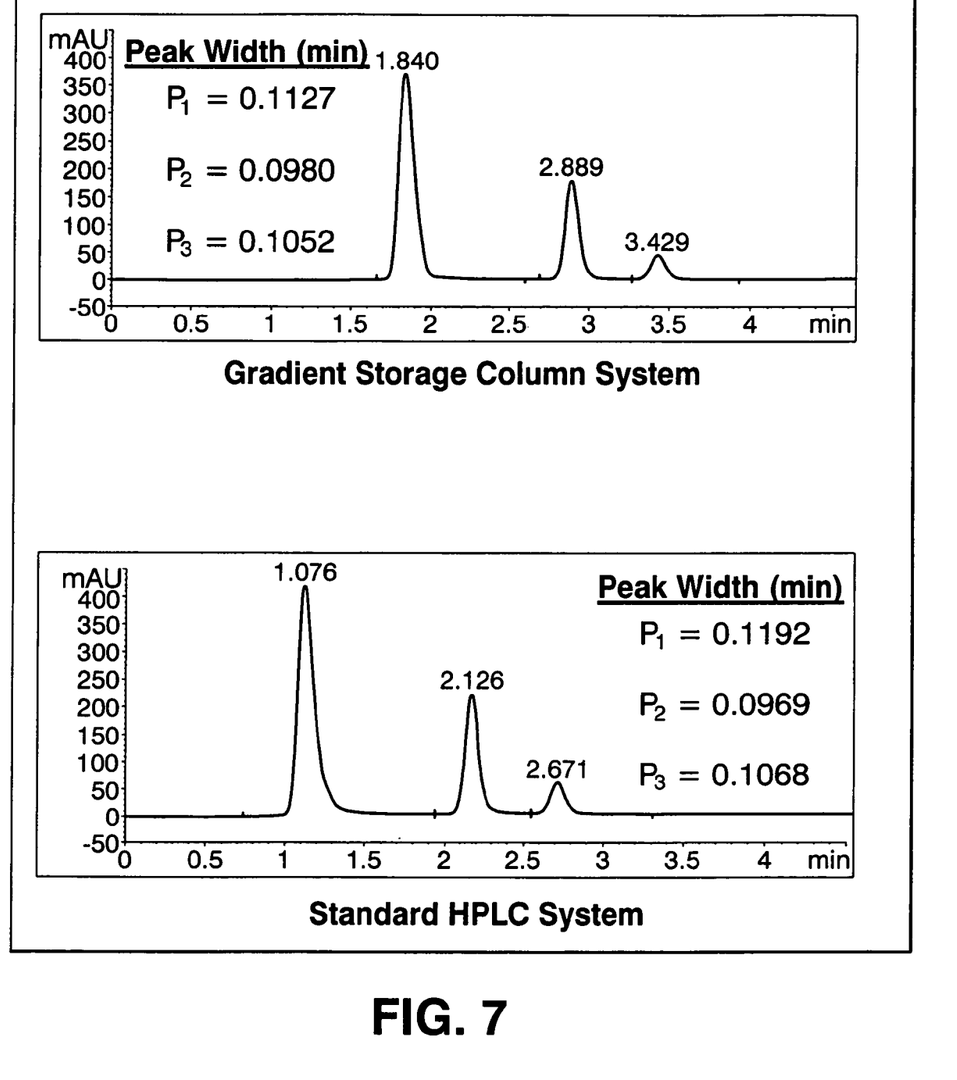
FIG. 7 is a schematic graph showing the chromatographic separation results of the identical solvent composition using the present gradient storage column system and an unmodified commercial HPLC system.

FIG. 7 illustrates the chromatographic separation results of the identical analyses of urasil, acetophenone, and methyl benzoate using the gradient storage column system and an unmodified commercial HPLC system. In both cases the same analytical column, namely, a Polaris, 5 micron C-18-A. A 60% acetonitril/40% water mobile phase was chosen, a flow rate of 0.2 mL/min was selected as well as a 2 microliter injection volume. Comparison of the peak widths of two chromatograms indicates that no deleterious effects appear to be associated with loading the injection plug onto the gradient storage column before starting the analysis. It will be understood that although these results were obtained at standard pressures, similar results should be realized at ultra high pressures. Thus, the construction and use of a gradient storage column 300 was verified as being suitable for use as a means for receiving and storing a gradient or mobile phase before loading the stored gradient onto the main analytical column 110.

One of the advantages of the gradient storage column is that by being located in a post injector position and by being in communication with standard HPLC pumps, such as pumps 112, 114, and the ultra-high pressure pump 250, the gradient and injection plug are treated with two vastly different pressure schemes depending on whether the injection plug is being loaded onto the gradient storage column or whether the injection plug is being transported from the gradient storage column for loading on the standard analytical column. More specifically, the gradient and injection plug are loaded under normal pressures onto the gradient storage column, while they are transported from the gradient storage column to the analytical column under ultra-high pressure by means of the ultra-high pressure pump.

The conversion kit aspect of the present UHPLC module 210 provides a number of disadvantages, including that the UHPLC module 210 can be retrofitted to any existing system. Thus, one does not have to buy expansive replacement injector and/or pumps when UHPLC performance is desired. In addition, the UHPLC module 210 can easily be removed from the equipment of a conventional HPLC system by simply disconnecting a conduit and/or by simply replacing a valve or the UHPLC module 210 can be taken "off-line" by placing the switching valve 230 or the check valve 200 in a position or setting that prevents any fluid (e.g., injection plug) from being delivered to the gradient storage column 300.

It will be appreciated by persons skilled in the art that the present invention is not limited to the embodiments described thus far with reference to the accompanying drawings; rather the present invention is limited only by the following claims.

What is claimed is:

1. An ultra-high pressure chromatography system (UHPLC) comprising:
   a high pressure chromatography arrangement of equipment including:
      at least one solvent reservoir maintaining an associated solvent, the number of solvent reservoirs being equal to the number of solvents;
      at least one high pressure pump that is operatively coupled to the at least one solvent reservoir for transporting the solvent;

an injector disposed downstream of the at least one solvent reservoir for receiving the associated solvent or a gradient formed as a mix of several solvents; and at least one analytical column disposed downstream of the injector for performing separation on an injection plug that is delivered thereto by the injector, a first conduit being disposed between the injector and the at least one analytical column; and a UHPLC module for converting the high pressure chromatography arrangement of equipment into the UHPLC system, the module including:

a first valve disposed within the first conduit;

a gradient storage column fluidly connected to the first conduit and operatively coupled to the first valve so that the injection plug can be selectively delivered and stored therein; and an ultra-high pressure pump operatively connected to the gradient storage column for loading the stored injection plug onto the analytical column for separation thereof;

wherein during loading of the injection plug onto the analytical column, the high pressure chromatography arrangement of equipment upstream of the first valve is shielded from ultra-high pressures generated by the ultra-high pressure pump.

2. The UHPLC of claim 1, wherein the first valve is positionable between an open position and a closed position, wherein in the open position, fluid communication is provided between the injector and the gradient storage column and in the closed position, fluid communication is prevented between the injector and the gradient storage column, thereby isolating and placing the gradient storage column in fluid communication with the analytical column.

3. The UHPLC of claim 2, wherein the first valve comprises a check valve.

4. The UHPLC of claim 1, wherein the at least one high pressure pump operates at pressures of less than 5,000 psi.

5. The UHPLC of claim 1, wherein there are at least two solvent reservoirs and at least two high pressure pumps, each solvent reservoir being operatively connected to one high pressure pump for transporting one solvent to the injector.

6. The UHPLC of claim 5, wherein the at least two high pressure pumps generate the gradient that is a mixture of the solvents at prescribed concentration ratios over time and is delivered to the injector.

7. The UHPLC of claim 1, wherein the first valve comprises an ultra-high pressure valve that is constructed to withstand and operate in an ultra-high pressure environment with pressures of greater than 5,000 psi.

8. The UHPLC of claim 7, wherein the ultra-high pressure valve operates in an ultra-high pressure environment defined by pressures greater than 5,000 psi and less than 60,000 psi.

9. The UHPLC of claim 1, wherein the gradient storage column comprises a column that is shaped into a plurality of adjacent loops for minimizing physical space taken up thereby.

10. The UHPLC of claim 1, wherein the gradient storage column has a minimum storage capacity of 2 mL.

11. The UHPLC of claim 1, wherein the gradient storage column has an inner diameter of about 0.01 inches.

12. The UHPLC of claim 1, wherein the gradient is stored inverted in the gradient storage column compared to the makeup of the gradient when loaded onto the analytical column.

13. The UHPLC of claim 1, wherein the first valve is a multi-port valve that can operate at pressures equal to and greater than 20,000 psi.

14. The UHPLC of claim 1, wherein the at least one ultra-high pressure pump operates at pressures of greater than 5,000 psi.

15. The UHPLC of claim 1, wherein the at least one ultra-high pressure pump operates at pressures greater than 5,000 psi and less than 60,000 psi.

16. The UHPLC of claim 1, wherein the first valve is a check valve disposed in the first conduit for isolating the HPLC equipment from ultra-high pressures generated by the ultra-high pressure pump, thereby preserving integrity of the HPLC equipment during loading of the injection plug into the analytical column from the gradient storage column, wherein in the open position, the injection plug is drawn into the gradient storage column by means of back pressures generated therein.

17. The UHPLC of claim 1, further including:

a detector downstream of the analytical column and fluidly connected thereto.

18. The UHPLC of claim 1, wherein the first valve comprises one of a switching valve and a tee.

* * * * *